United States Patent
Flora et al.

(10) Patent No.: US 6,752,817 B2
(45) Date of Patent: Jun. 22, 2004

(54) SPLIT PRESSURE RING FOR LANCING DEVICE AND METHOD OF OPERATION

(75) Inventors: Bruce A. Flora, Goshen, IN (US); Robert C. Whitson, Goshen, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 10/078,519

(22) Filed: Feb. 20, 2002

(65) Prior Publication Data

US 2002/0138040 A1 Sep. 26, 2002

Related U.S. Application Data

(60) Provisional application No. 60/278,537, filed on Mar. 26, 2001.

(51) Int. Cl.[7] ............................................. A61B 17/14
(52) U.S. Cl. ..................................... 606/181; 600/583
(58) Field of Search .............................. 606/181, 182, 606/184, 185, 186, 188, 167, 172, 183; 600/583

(56) References Cited

U.S. PATENT DOCUMENTS

| | | | | |
|---|---|---|---|---|
| 3,855,745 A | * | 12/1974 | Patterson et al. ............. 52/159 |
| 4,377,945 A | * | 3/1983 | Di Giovanni et al. ... 73/40.5 R |
| 4,644,617 A | * | 2/1987 | Tupper et al. ................. 24/611 |
| 4,653,513 A | * | 3/1987 | Dombrowski ................ 600/578 |
| 5,161,317 A | * | 11/1992 | McDougall .................... 34/97 |
| 5,324,303 A | * | 6/1994 | Strong et al. ................. 606/181 |
| 5,383,885 A | * | 1/1995 | Bland ........................... 606/182 |
| 5,395,387 A | * | 3/1995 | Burns ........................... 606/181 |
| 5,403,132 A | * | 4/1995 | Truesdell ....................... 409/131 |
| 5,571,132 A | * | 11/1996 | Mawhirt et al. .............. 606/182 |
| 5,613,978 A | * | 3/1997 | Harding ........................ 606/181 |
| 5,660,791 A | * | 8/1997 | Brenneman et al. ............ 422/58 |
| 5,831,217 A | * | 11/1998 | Jarvis et al. ............... 174/153 R |
| 5,879,311 A | * | 3/1999 | Duchon et al. .............. 600/583 |
| 6,022,366 A | * | 2/2000 | Schraga ........................ 606/181 |
| 6,056,701 A | * | 5/2000 | Duchon et al. .............. 600/583 |
| 6,197,040 B1 | * | 3/2001 | LeVaughn et al. ............ 606/182 |
| 6,277,083 B1 | * | 8/2001 | Eggers et al. ................ 600/564 |
| 6,451,040 B1 | * | 9/2002 | Purcell ......................... 606/181 |
| 6,508,822 B1 | * | 1/2003 | Peterson et al. ............. 606/153 |
| 6,537,242 B1 | * | 3/2003 | Palmer .......................... 604/22 |

FOREIGN PATENT DOCUMENTS

WO    WO 0074763    * 12/2000    .................. 606/182

* cited by examiner

Primary Examiner—Kevin T. Truong
Assistant Examiner—Vi X Nguyen
(74) Attorney, Agent, or Firm—Jerome L. Jeffers; Alice A. Brewer

(57) ABSTRACT

A pressure ring for a lancing device for holding open a skin puncture while collecting a blood sample includes a collar that fits onto the end of a lancing device. A skirt is provided on the collar and a flared portion depends from the skirt. At least one axial slit is formed in the skirt. The pressure ring is made of a flexible material such as polypropylene such that when the lancing device with a pressure ring is placed on a person's skin and pressure is applied, the slits spread apart stretching the skin for a puncture by a lance in the lancing device. Once a puncture has been made, the pressure ring holds the puncture wound open to allow bleeding. Removing the lancing device from the puncture site releases the skin allowing the puncture wound to close.

20 Claims, 1 Drawing Sheet

SPLIT PRESSURE RING FOR LANCING DEVICE AND METHOD OF OPERATION

This application claims the benefit of Provisional Application No. 60/278,537 filed Mar. 26, 2001.

FIELD OF THE INVENTION

The present invention generally relates to a split pressure ring for a lancing device and, more particularly, to a pressure ring with at least one slit that is pressed against skin causing the split in the ring to spread apart thereby tightening the skin for a puncture and drawing of a blood sample.

BACKGROUND OF THE INVENTION

Many people for health reasons are required to test their blood several times a day. For example, diabetics must frequently test the level of glucose in their blood throughout each day. To perform these tests a sample of blood is needed and this is typically collected by a lancing device and tested by a glucometer. The lancing device drives a lance into the skin to form a puncture wound. The lancing device is then removed and the user manually squeezes or massages the puncture site until enough blood is obtained to perform a test. It is desirable to eliminate the need for a user to squeeze or massage the puncture site to obtain blood since squeezing or massaging can cause discomfort. One example of a device seeking to avoid the manual squeezing is provided by Amira Medical in Scotts Valley, Calif. They sell the AtLast blood glucose system. This system includes a rigid tube used with a press and release motion to draw blood to the surface of the puncture. Another example is a product called Thera Sense Free Style made by Tera Sense in Alameda, Calif. This is a blood glucose monitoring system which includes a lancing device with a molded pressure ring that is part of an end cap on the lancing device. The molded pressure ring is not split.

SUMMARY OF THE INVENTION

The present invention provides a device for and a method of drawing blood from a puncture site. The device is a split pressure ring that fits on an end of a lancing device. The split pressure ring includes a collar that encircles an end of a lancing device. The split pressure ring further includes a skirt extending from the collar and into a linear or curvilinear flared portion. The flared portion is terminated by a rim and at least one slit is formed in the rim and the flared portion. The split pressure ring is formed of a flexible material and this with the slit allows the pressure ring to flex and the slit to spread when force is applied. Thus, when the pressure ring is pressed against skin at a puncture site, the ring deforms causing the slit to spread apart and stretch the skin for lancing and to draw blood after the skin has been lanced.

BRIEF DESCRIPTION OF THE DRAWINGS

Other objects and advantages of the invention will become apparent upon reading the following detailed description and upon reference to the drawings in which.

Figure 1:
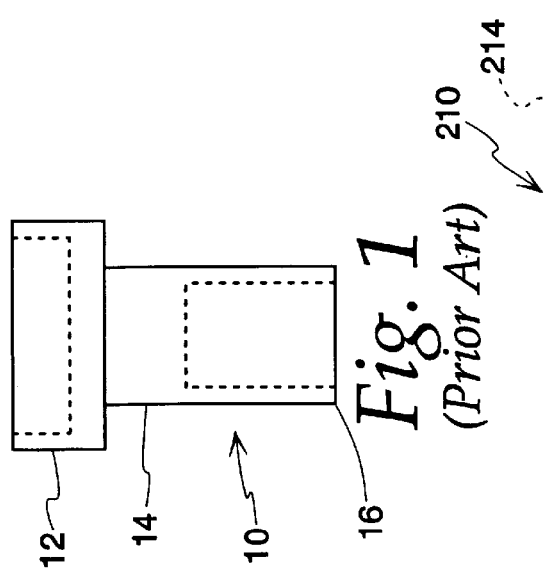
FIG. 1 is a front elevation view of a prior art rigid tube pressure ring.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENTS

A prior art rigid tube pressure ring 10 is illustrated in FIG. 1. The rigid tube pressure ring 10 is of the type used in the Amira Medical AtLast blood glucose system. The rigid tube pressure ring 10 includes a collar 12 that fits onto a lancing device (not shown). A straight skirt 14 extends from the collar 12. The rigid tube pressure ring 10 is formed of an inflexible material. To obtain a sample of blood, a lower end 16 of the skirt 14 is pressed on the skin around a puncture and a press and release motion draws blood to the surface. The inflexibility of the rigid tube pressure ring 10 is uncomfortable to the user and does not quickly and easily draw sufficient blood needed for testing.

Figure 4:
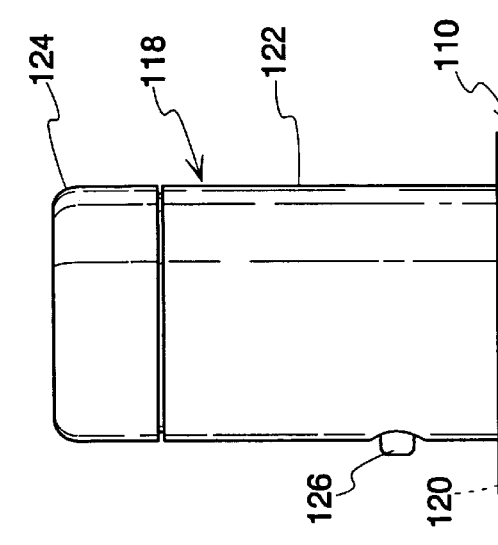
FIG. 4 is plan view of the split pressure ring of FIGS. 2–3 mounted on a lancing device.
Figure 3:
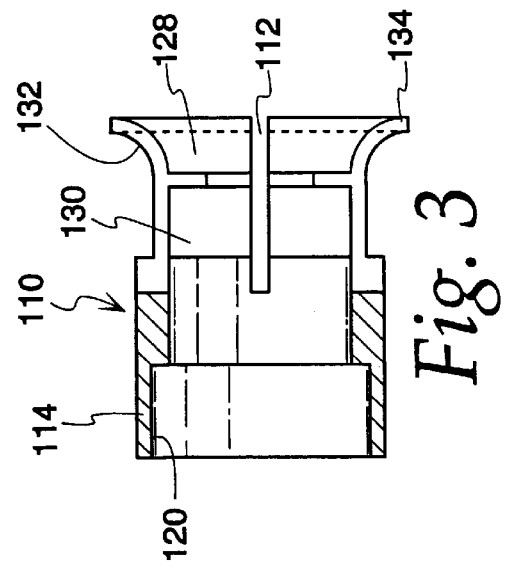
FIG. 3 is a view taken along line 3—3 of FIG. 2.
Figure 2:
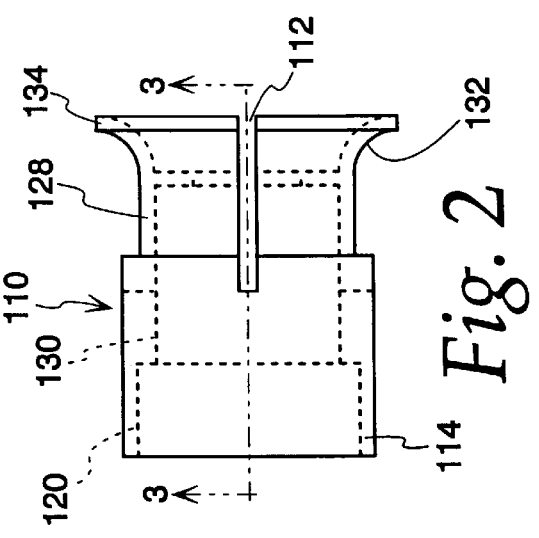
FIG. 2 is a plan view of a split pressure ring constructed in accordance with the principles of the present invention.

The split pressure ring 110 illustrated in FIGS. 2–4 overcomes these deficiencies by being flexible and functioning differently. The flexibility of the split pressure ring 110 is provided by the material from which the split pressure ring 110 is formed and the inclusion of one or more longitudinal slits 112 extending parallel to the central axis of the split pressure ring 110. The split pressure ring 110 functions by the slits 112 spreading apart when the split pressure ring 110 is placed on a puncture site and axial pressure is applied. This spreading apart of the slits 112 stretches the skin before puncture and holds the wound open after puncture until enough sample bleeds from the wound for testing.

The split pressure ring 110 includes a collar 114 that fits over an end 116 of a lancing device 118. The collar 114 includes a central bore 120 that fits over and around the end 116 of the lancing device 118.

The lancing device 118 includes a body 122 that houses a lance and a driving mechanism for driving the lance out of the end 116 and into skin at a puncture site. The driving mechanism is cocked by a top or knob 124 on the body 122 and is released to drive the lance by a button 126.

The split pressure ring 110 includes a skirt 128 extending from the collar 114. The collar 114 and the skirt 128 have a central passage 130 along which the lance is driven. A flared portion 132 terminating in a rim 134 extends form the skirt 128. The flared portion 132 is curvilinear and, in a preferred embodiment, at a radius of approximately 0.095 inch. This radius adds flexibility to the flared portion 132 but other radii can be used.

The entire split pressure ring 110 and in particular the skirt 128, the flared portion 132 and the rim 134 are formed of flexible material such as polypropylene or DELRIN®. In addition, the four longitudinal slits 112 spaced approximately 90° apart are formed in the rim 134, the flared portion 132, the skirt 128 and part of the collar 114. The flexible material and the slits 112 provide a flexible split pressure ring 110 in which the slits 112 spread apart and the split pressure ring 110 slides along its central axis as a controlled axial force is applied to the split pressure ring 110.

To use the blood drawing system defined by the lancing device 118 and the split pressure ring 110, the end 116 of the lancing device 118 is inserted into the central bore 120 of the collar 114. The assembled blood drawing system is placed on a puncture site by placing the rim 134 on the skin of a user or patient. A controlled force is applied to the split pressure ring 110 pressing the lancing device 118 toward the puncture site. This controlled force causes deformation of the skirt 128, the flared portion 132 and the rim 134 and spreads apart the slits 112. This deformation and spreading stretches the skin at the puncture site. The driving mechanism of the lancing device 118 is activated by pressing the button 126 and the lance is driven out of the end 116 of the lancing device 118, along the passage 130 and into the stretched skin of the user. The lance is withdrawn and the controlled force on the split pressure ring 110 is maintained thereby holding the puncture wound open. Once enough sample has bled from the puncture wound, the controlled force is released and the blood drawing system is lifted from the puncture site allowing the wound to close and begin healing. A sensor, test strip or other device may be applied to the sample for testing.

Figure 5:
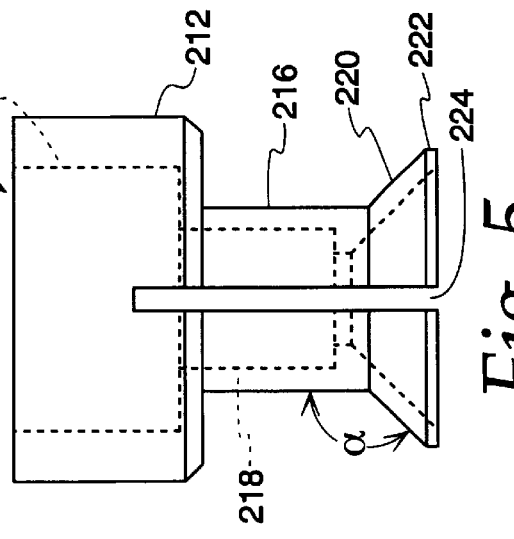
FIG. 5 is a plan view of an alternative embodiment of the split pressure ring illustrated in FIGS. 2–4.

An alternative embodiment of the split pressure ring 110 is illustrated in FIG. 5. The alternative split pressure ring 210 is similar to the split pressure ring 110 in that it includes a collar 212, a central bore 214 in the collar 212, a skirt 216 depending from the collar 212, and a passage 218 extending through the skirt 216. The alternative split pressure ring 210 differs from the split pressure ring 110 in that it includes a linear. flared portion 220 that terminates in a rim 222. The angle α of the linear flared portion 220 is approximately 135°.

The alternative split pressure ring 210 is made of the same flexible material as the split pressure ring 110 and includes longitudinal slits 224 in the rim 222, linear flared portion 220, skirt 216 and part of the collar 212. With this material and structure the alternative split pressure ring 210 operates in the same way as the split pressure ring 110.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. An apparatus for lancing the skin of a test subject, comprising:
   a lancing device for puncturing skin; and
   a pressure ring having a collar configured to fit on an end of the lancing device, the pressure ring including a skirt on said collar and a flared potion flaring from said skirt for contacting skin, the pressure ring including at least one longitudinal slit in said flared portion.

2. The apparatus claimed in claim 1 comprising four equally spaced longitudinal slits in said skirt.

3. The apparatus claimed in claim 1 said flared portion being linear.

4. The apparatus claimed in claim 1 said flared portion being linear and at an angle of about 135° to the longitudinal axis of said skin pressure ring.

5. The apparatus claimed in claim 1 said flared portion being curvilinear.

6. The apparatus claimed in claim 1 said flared portion being curvilinear and of a radius of about 0.095 inch.

7. The apparatus claimed in claim 1 comprising a rim on said flared portion.

8. The apparatus claimed in claim 1 said collar, skirt and flared portion formed of polypropylene.

9. The apparatus claimed in claim 1 said collar, skirt and flared portion constructed of a flexible material.

10. A system for drawing blood, comprising:
    a lancing device including a first end, a lance mounted in said lancing device, a lance driver in said lancing device for driving said lance out of said first end, and
    a pressure ring mounted on said first end of said lancing device, said pressure ring including a collar, a skirt extending from said collar, a flared portion extending from said skirt, and at least one slit in said flared portion.

11. The system claimed in claim 10 said at least one slit extending parallel to a central axis of said pressure ring.

12. The system claimed in claim 10 comprising four slits extending through said flared portion and said skirt equally spaced around said pressure ring.

13. The system claim in 10 said flared portion being linear.

14. The system claim in 10 said flared portion being curvilinear.

15. The system claim in 10 said flared portion being polypropylene.

16. The system claimed in claim 10 said pressure ring constructed of a flexible material.

17. The system claimed in claim 10 said pressure ring including a rim on said flared portion.

18. The system claimed in claim 10 said at least one slit extending at least partially into said collar.

19. A method of applying pressure on a puncture site of a lancing device, said lancing device including a body with a first end, a lance in said body and a driver for driving said lance out of said first end, a lance in said body and a driver for driving said lance out of said first end and into a puncture site, a pressure ring mounted on said first end of said body of said lancing device, said pressure ring including a skirt and flared portion and at least one slit in said flared portion, comprising:
    placing the flared portion of said pressure ring on a puncture site; and
    applying force on said pressure ring to deform at least said flared portion of said pressure ring.

20. The method of applying pressure on a puncture site claimed in claim 19 comprising:
    driving said lance into said pressure site; and
    maintaining said force on said pressure ring until sufficient sample is drawn from said puncture site.

* * * * *